United States Patent

Yoshimura (10) Patent No.: US 9,693,703 B2
(45) Date of Patent: Jul. 4, 2017

(54) ELECTROCARDIOGRAM DISPLAY DEVICE (71) Applicant: NIHON KOHDEN CORPORATION, Tokyo (JP)

(72) Inventor: Hisao Yoshimura, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 14/868,378

(22) Filed: Sep. 28, 2015

(65) Prior Publication Data

US 2016/0095526 A1 Apr. 7, 2016

(30) Foreign Application Priority Data

Oct. 3, 2014 (JP) ................. 2014-204565

(51) Int. Cl.
A61B 5/04 (2006.01)
A61B 5/044 (2006.01)

(52) U.S. Cl.
CPC .......... *A61B 5/044* (2013.01); *A61B 5/04012* (2013.01)

(58) Field of Classification Search
CPC .... A61B 5/044; A61B 5/04012; A61B 5/0432
USPC ........................................................ 600/523
See application file for complete search history.

(56) References Cited

U.S. PATENT DOCUMENTS

2009/0192400 A1 7/2009 Kamataki
2010/0261979 A1* 10/2010 Kiani ................... A61B 5/0002 600/301
2015/0141862 A1* 5/2015 Montambeau ......... A61B 5/748 600/523

FOREIGN PATENT DOCUMENTS

JP 5196296 B2 2/2013

* cited by examiner

Primary Examiner — Amanda Patton
Assistant Examiner — Philip C Edwards
(74) Attorney, Agent, or Firm — Pearne & Gordon LLP (57) ABSTRACT An electrocardiogram display device includes an electrocardiogram waveform generating unit that generates electrocardiogram waveforms of a plurality of leads based on electrocardiogram data of each of the leads, an arranging instruction unit that instructs an arranging order of the electrocardiogram waveform of each lead by performing inputting, a display unit, and a displaying control unit that arranging the electrocardiogram waveform of each lead in a corresponding arranging order in response to instruction of the arranging instruction unit to create and display one screen image on the display unit.

15 Claims, 10 Drawing Sheets

| CASE NAMES | CHARACTERISTICS OF ELECTROCARDIOGRAM WAVEFORM | ARRANGING-ORDER CANDIDATES |
|---|---|---|
| ATRIOVENTRICULAR NODAL RHYTHM | INVERSION OF POLARITY IN A P-WAVE AFTER -aVR | CABRERA LEAD |
| MYOCARDIAL INFARCTION | ST LEVEL IS CHANGED IN THE VICINITY OF A LESION SITE IN ACCORDANCE WITH AN ARRANGING ORDER | CABRERA LEAD |
| ............ | ............ | ............ |

FIG. 10 ic signals at predetermined sites of the patient can be obtained. In the presently disclosed subject matter, a kind of the electrocardiogram signals is not specifically limited.

ELECTROCARDIOGRAM DISPLAY DEVICE

CROSS REFERENCE TO RELATED APPLICATION

This application is based on Japanese Patent Applications No. 2014-204565 filed on Oct. 3, 2014, the contents of which are incorporated herein by reference.

BACKGROUND

The presently disclosed subject matter relates to an electrocardiogram display device in which a measured electrocardiogram waveform of each of a plurality of leads can be used to appropriately change and display an arrangement of the electrocardiogram waveform of each lead.

Conventionally, an electrocardiogram display device is generally known in which electrocardiogram is displayed in an arranging order in accordance with standard 12-lead mode. On the other hand, as a lead displaying mode, which employs a method of vectorially displaying extremity leads, Cabrera lead mode is known.

However, in any case, depending on an initial setting, electrocardiogram display devices become an electrocardiogram display device, in which electrocardiogram is displayed in an arranging order in accordance with standard 12-lead mode, or an electrocardiogram display device in accordance with Cabrera lead mode employing a method of vectorially displaying extremity leads. In other words, so long as the setting is not changed, a display mode is fixed.

For example, in Japanese Patent No. 5196296, it is described that displaying is not limited to a displaying order in accordance with 12-lead mode, but a simple arrangement in order of I to III, V1 to V6 and the like, or an arrangement conscious of the Cabrera lead mode is enabled. However, the description of Japanese Patent No. 5196296 does not explain that displaying in a displaying order of standard 12-lead mode can be switched into displaying in accordance with Cabrera lead mode.

Namely, it is only explained that a displaying order shown in FIG. 2 of Japanese Pat. No. 5,196,296 as an example of a screen image for batch displaying is just an example.

Therefore, when displaying in accordance with standard 12-lead mode is performed as described above, thought work by a doctor or the like which changes the displaying order in his head or the like are required because the displaying order is fixed even if attempting to vectorially capture an firing procedure of myocardium to understand the electrocardiogram.

In addition, even if attempting to change an order of leads to understand the electrocardiogram during thought, this cannot be easily performed, but requires training and a lot of time to acquire skills.

The presently disclosed subject matter has been made keeping in mind such current situations of electrocardiogram display devices, and an object thereof is to provide an electrocardiogram display device which can appropriately change and display an arrangement of an electrocardiogram waveform of each lead from one, which is currently displayed, to another.

SUMMARY

An electrocardiogram display device includes an electrocardiogram waveform generating unit that generates electrocardiogram waveforms of a plurality of leads based on electrocardiogram data of each of the leads, an arranging instruction unit that instructs an arranging order of the electrocardiogram waveform of each lead by performing inputting, a display unit, and a displaying control unit that arranging the electrocardiogram waveform of each lead in a corresponding arranging order in response to instruction of the arranging instruction unit to create and display one screen image on the display unit.

BRIEF DESCRIPTION OF DRAWINGS

FIGS. 6A and 6B are views showing an example of one screen image changed by displaying candidates shown in FIG. 5, where FIG. 6A shows a display example prior to changing and FIG. 6B shows a display example after changing.

DETAILED DESCRIPTION OF EMBODIMENTS

Figure 1:
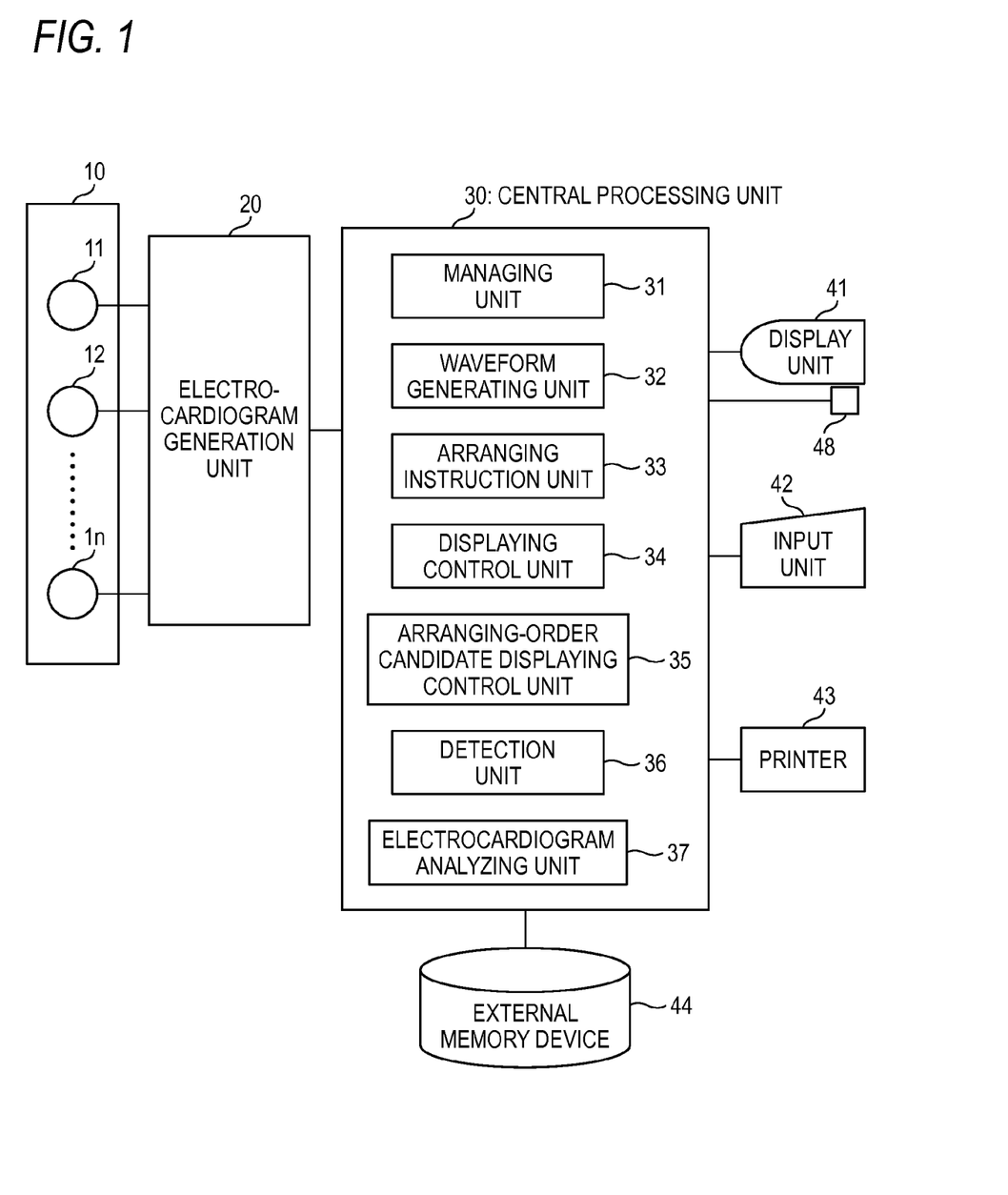
FIG. 1 is a block diagram showing configurations of an embodiment of an electrocardiogram display device according to the presently disclosed subject matter.

Embodiments of an electrocardiogram display device according to the presently disclosed subject matter will be now described with reference with the accompanying drawings. The same components in the figures are designated by the same reference numerals and the overlapped descriptions thereof will be omitted. FIG. 1 is a configuration view of an embodiment of the electrocardiogram display device according to the presently disclosed subject matter. The electrocardiogram display device have an electrode group 10 constituted of electrodes 11 to 1n, and an electrocardiogram generation unit 20 for obtaining electrocardiogram data from electrocardiogram signals obtained by the electrode group 10.

In the foregoing, the electrodes 11 to 1n are attached to predetermined known sites on a patient, so that an electrocardiogram can be obtained. The electrocardiogram generation unit 20 is intended to generate multi-lead electrocardiogram data by appropriately combining signals obtained from the electrodes 11 to 1n.

To the electrocardiogram generation unit 20, a central processing unit 30 constituted of, for example, a computer is connected. The multi-lead electrocardiogram signals obtained from the electrodes 11 to 1n are A/D-converted in the electrocardiogram generation unit 20.

To the central processing unit 30, a display unit 41 for displaying information, an input unit 42 constructed by a keyboard or a mouse for inputting information, a printer 43 for printing information, an external memory device 44 for storing information, and the like are connected. The input unit 42 may be constructed by a touch panel provided on a screen of the display unit 41.

The central processing unit 30 has a managing unit 31, a waveform generating unit 32 for generating a waveform of each lead, an arranging instruction unit 33, a displaying control unit 34, an arranging-order candidate displaying control unit 35, a detecting unit 36 for detecting whether a screen is arranged to be vertically or horizontally long, and an electrocardiogram analyzing unit 37. Each of these units is embodied by executing programs by the central processing unit 30 as a computer.

The managing unit 31 is intended to manage the waveform generating unit 32, the arranging instruction unit 33, the displaying control unit 34, the arranging-order candidate displaying control unit 35, the detecting unit 36 and the electrocardiogram analyzing unit 37 and is configured to perform causing the waveform generating unit 32 to process electrocardiogram obtained from the electrocardiogram generation unit 20, storing the results into the external memory device 44 and the like. Alternatively, the managing unit 31 controls to send information of an arranging order, which is initially set, and a selection input, which is received from the arranging instruction unit 33 afterward, to the displaying control unit 34 and then manages to display an image created by the displaying control unit 34 on the display unit 41.

The waveform generating unit 32 is intended to generate an electrocardiogram waveform of each of a plurality of leads based on the electrocardiogram data obtained from the electrocardiogram generation unit 20. The arranging instruction unit 33 is intended to instruct an arranging order of the electrocardiogram waveform of each lead, and the instruction can be performed in accordance with an input or on the basis of electrocardiogram analysis results.

The displaying control unit 34 is intended to arrange the electrocardiogram waveform of each lead in a corresponding arranging order in response to instruction of the arranging instruction unit 33 to create and display one screen image on the display unit 41.

The electrocardiogram analyzing unit 37 is intended to sort the inputted electrocardiogram waveforms in accordance with an analyzing program. Also, on the basis of the sorted electrocardiogram waveforms, the electrocardiogram analyzing unit 37 determines arranging-order candidate information for the electrocardiogram waveform of each lead optimized to examine one or more prioritized case information and cases thereof. The arranging-order candidate displaying control unit 35 is intended to display the case information and the arranging-order candidate information in pairs on the display unit 41. In this case, the arranging instruction unit 33 may be configured to perform inputting for designating any one of the displayed case information and arranging-order candidate information.

The arranging-order candidate displaying control unit 35 is intended to display arranging-order candidate information of the electrocardiogram waveform of each lead on the display unit 41. In this case, the arranging instruction unit 33 may be configured to perform inputting for designating any one of the displayed arranging-order candidate information. Also, the arranging-order candidate displaying control unit 35 may be configured to display the case information and the arranging-order candidate information in pairs on the display unit 41.

The detecting unit 36 is intended to detect whether a screen of the display unit 41 is arranged to be vertically or horizontally long on the basis of an output of a sensor 48 provided on the screen of the display unit 41. If the screen is rotated about a rotation axis, the sensor 48 may be constructed by a senor for detecting a rotation angle of the rotation axis, a gyro-sensor or the like. In this case, the displaying control unit 34 may be configured to create and display one screen image, in which the electrocardiogram waveform of each lead is arranged in an arranging order changed depending on a result detected by the detecting unit 36, on the display unit 41.

Meanwhile, the electrocardiogram display device shown in FIG. 1 may be constructed by a single device as a whole or may be constructed by a plurality of devices separated in accordance with functions thereof. If the electrocardiogram display device is constructed by the plurality of devices, for example, the arranging instruction unit 33, the arranging-order candidate displaying control unit 35 and the detecting unit 36 of the central processing unit 30 can be constructed as separate devices. In this case, the electrocardiogram display device may include dedicated devices, personal computers or smart phones, and an electrocardiograph. The electrocardiogram analyzing unit 37 may be equipped in the electrocardiograph or may be equipped in a separate device.

Figure 2:
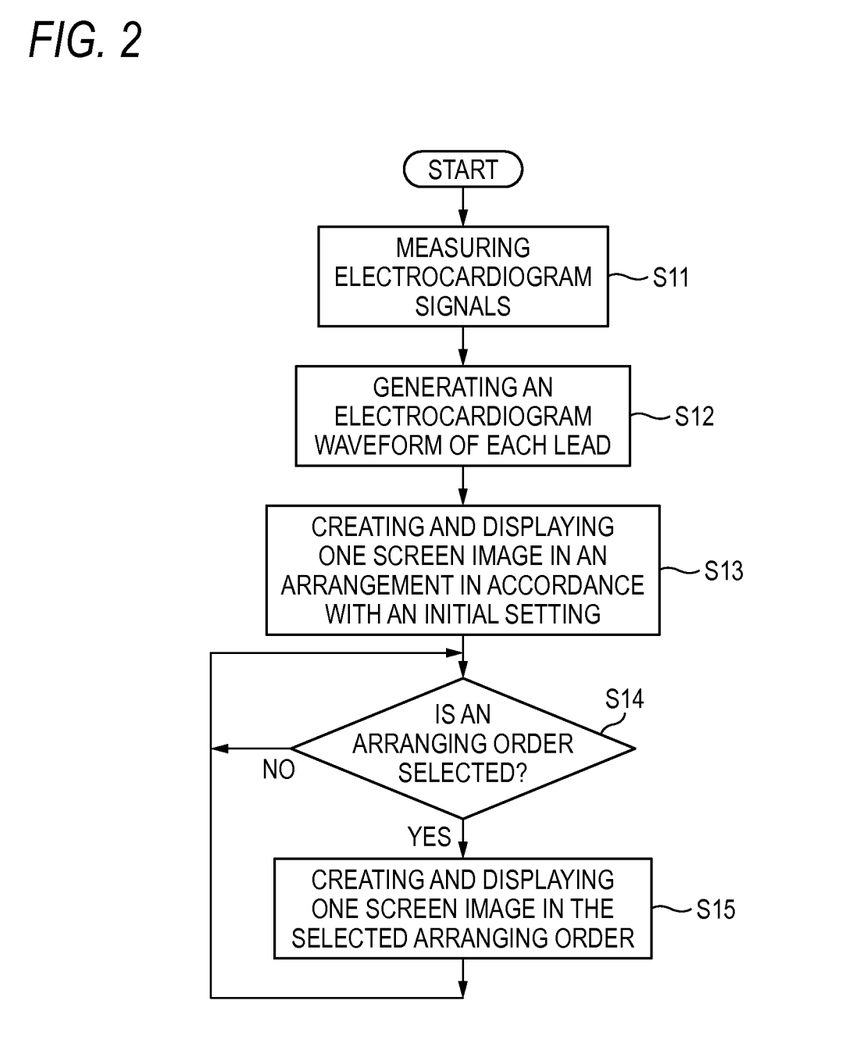
FIG. 2 is a flow chart showing operations of the embodiment of the electrocardiogram display device according to the presently disclosed subject matter.

The electrocardiogram display device configured as described above is operated, for example, as shown in a flow chart of the next FIG. 2. Herein, it is assumed that a displaying order of a standard 12-lead mode is set as an arranging order of an initial setting of the managing unit 31. When an inspection operator or the like attaches electrodes 11 to 1n at desired locations on extremity or chest of a patient and then instructs start of measuring through the input unit 42, measuring of electrocardiogram signals is performed (S11). The waveform generating unit 32 receives electrocardiogram data and then generates an electrocardiogram waveform of each of a plurality of leads (S12). Then, the managing unit 31 receives the arranging order of the initial setting and arranges the electrocardiogram waveform of each lead in an order in accordance with the standard 12-lead mode to create and display one screen image on the display unit 41 (S13).

Figure 3:
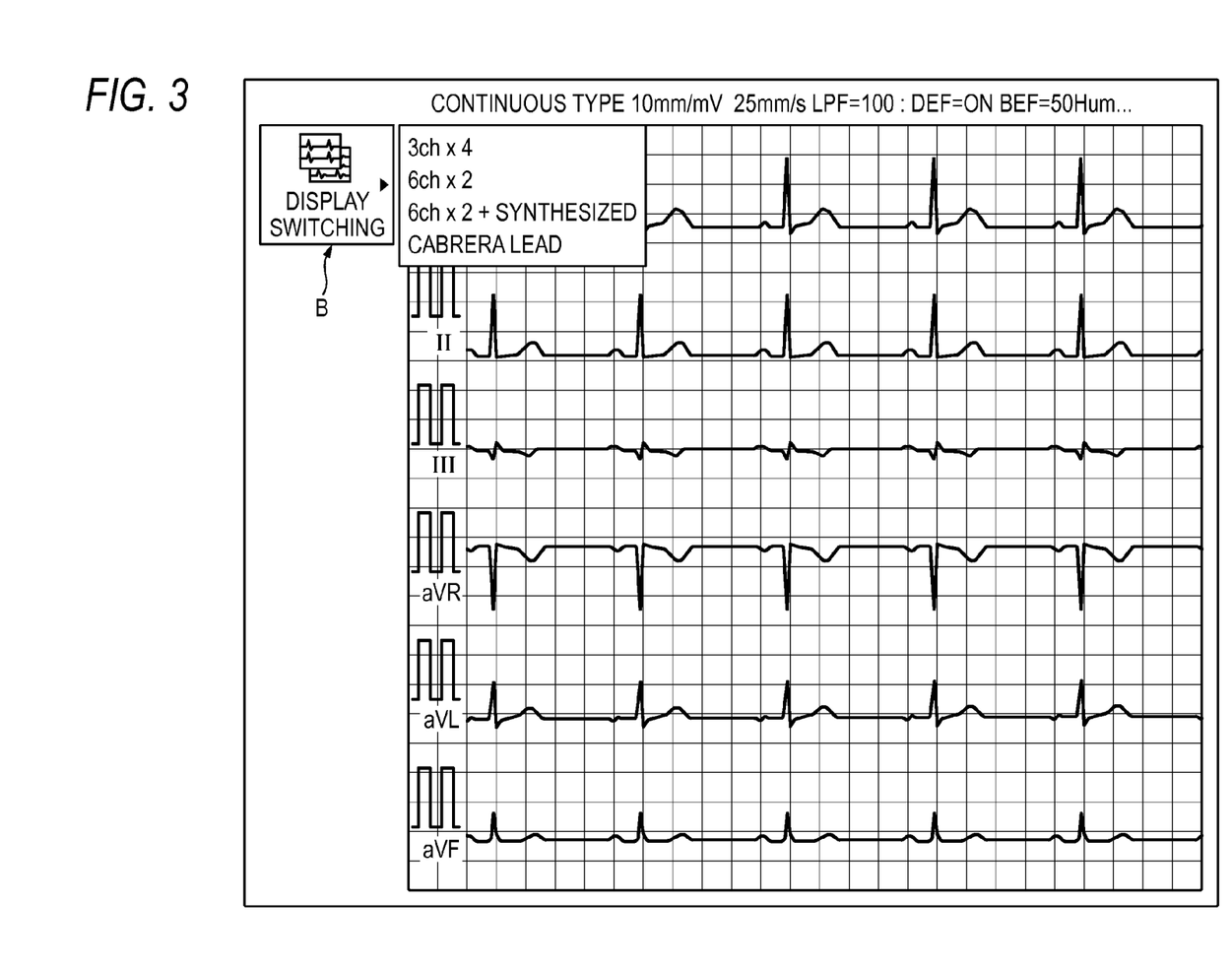
FIG. 3 is a view showing a display example of electrocardiogram waveforms and candidate information displayed by the embodiment of the electrocardiogram display device according to the presently disclosed subject matter.

In FIG. 3, an example of electrocardiogram arranged and displayed in an order in accordance with the standard 12-lead mode is shown. As shown, I lead, II lead, III lead, aVR lead, aVL lead and aVF lead are arranged from the top in this order, thereby constituting the one screen image.

Subsequently, whether or not selection by the arranging instruction unit 33 is performed is detected (S14). In the embodiment, if the electrocardiogram is displayed, as shown in FIG. 3, a "display switching" button B is displayed on a left upper corner of each screen. Thus, as an operator operates the "display switching" button B (e.g., operating by a touch panel or clicking by a mouse), arranging-order candidate information as presented on a pop-up window by the arranging-order candidate displaying control unit 35 is displayed.

In the example of FIG. 3, candidates, such as 3ch×4 lead mode displaying, 6ch×2 lead mode displaying, 6ch×2+ synthesized lead mode displaying and Cabrera lead mode displaying, are displayed. Alternatively, a lead mode, which is currently displayed, (herein, standard 12-lead mode displaying) may be also displayed in the candidates. In this case, in order to indicate that a candidate is one which is currently being displayed, the candidate may be displayed to be distinguished from the other candidates by an aspect (color or font) different from those of the others. If any one of the candidates is operated, the process is branched into YES at the step S14 to proceed to a step S15.

In the step S15, one screen image, in which the electrocardiogram waveform of each lead is arranged in an arranging order corresponding to the selected candidate, is created and displayed on the display unit 41 (S15).

Figure 4:
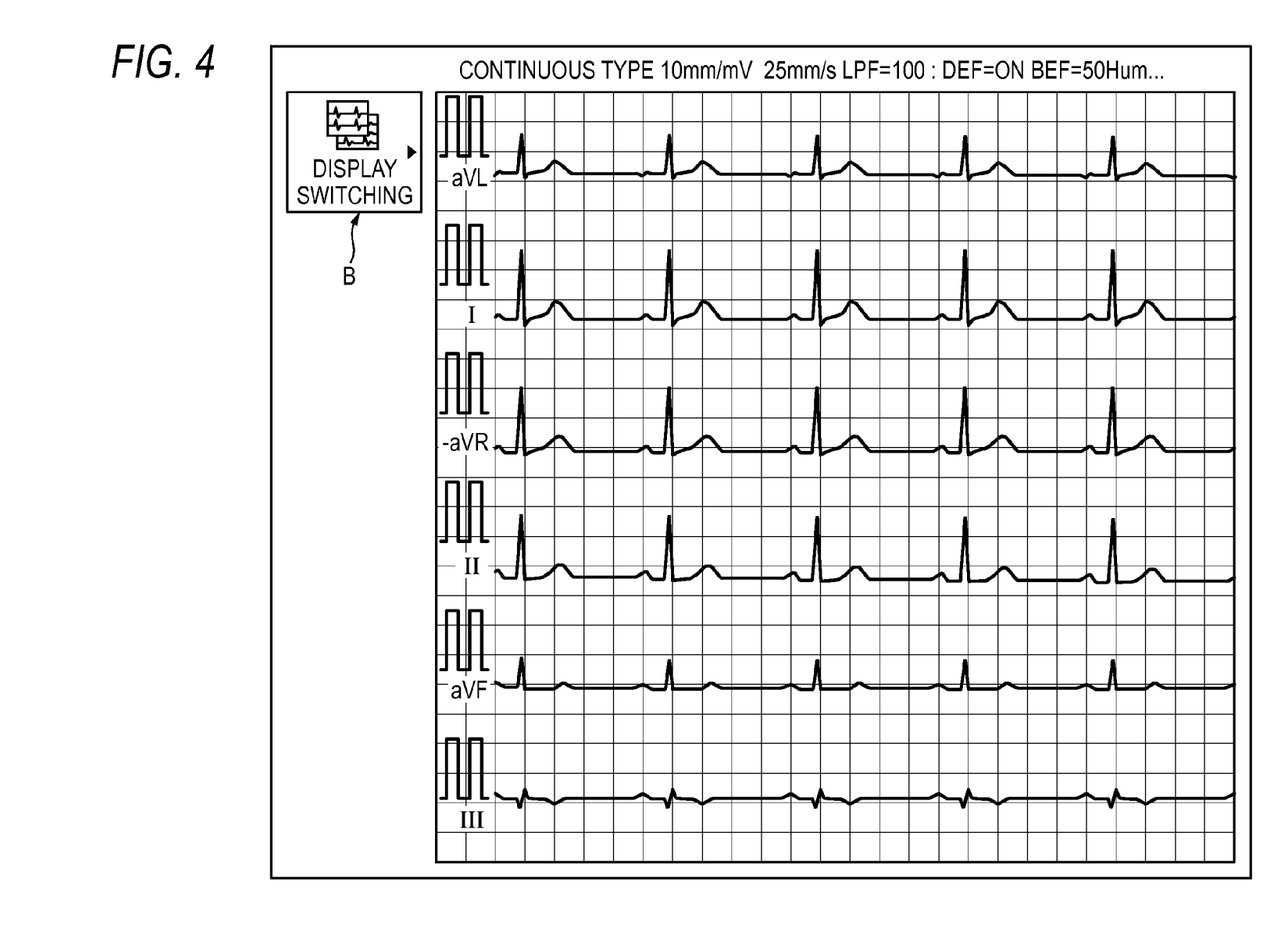
FIG. 4 is a view showing a display example changed from the display example of FIG. 4 by the embodiment of the electrocardiogram display device according to the presently disclosed subject matter.

In FIG. 4, an example in which the Cabrera lead mode is selected and thus the electrocardiogram is arranged and displayed in an order in accordance with the Cabrera lead mode is shown. As shown in FIG. 4, aVL lead, I lead, –aVR lead, II lead, aVF lead and III lead are arranged from the top in this order, thereby constituting the one screen image. When the processing of the step S15 is ended, the process returns to the step S14 and the processing thereof is continued. Thus, according to the present embodiment, arrangement of the electrocardiogram waveform of each lead can be appropriately changed and displayed from one which is currently being displayed.

Figure 5:
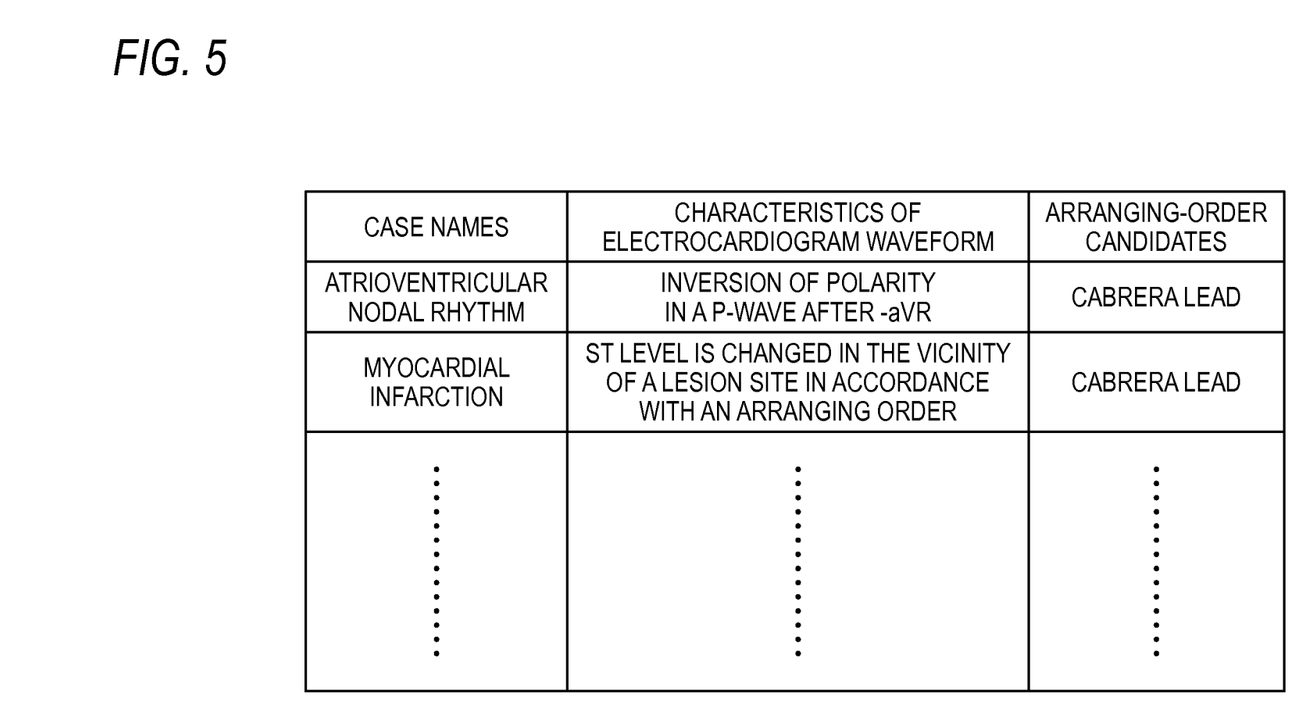
FIG. 5 is a view showing candidate information in which case information and arranging-order candidate information are displayed in pairs by the embodiment of the electrocardiogram display device according to the presently disclosed subject matter.

Next, a second embodiment will be described. In the second embodiment, the arranging-order candidate displaying control unit 35 displays arranging orders, which are suitable to examine and evaluate case information and cases thereof in detail, in pairs on the display unit 41 based on an analysis result of the electrocardiogram analyzing unit 37. In FIG. 5, an example of 'arranging-order candidate information' displayed by the arranging-order candidate displaying control unit 35 according to the second embodiment is shown. In this example, a case name, characteristics of electrocardiogram waveforms, and arranging-order candidates are displayed. Specifically, an "atrioventricular nodal rhythm" is set as the case name, "inversion of polarity in a P-wave after –aVR lead" is set as a characteristic of the electrocardiogram waveforms, and "Cabrera lead" is set as the arranging-order candidate. The arranging-order candidate information can be displayed on a pop-up window by displaying a button for calling the arranging-order candidate information on the screen and operating the button.

Figure 6A:
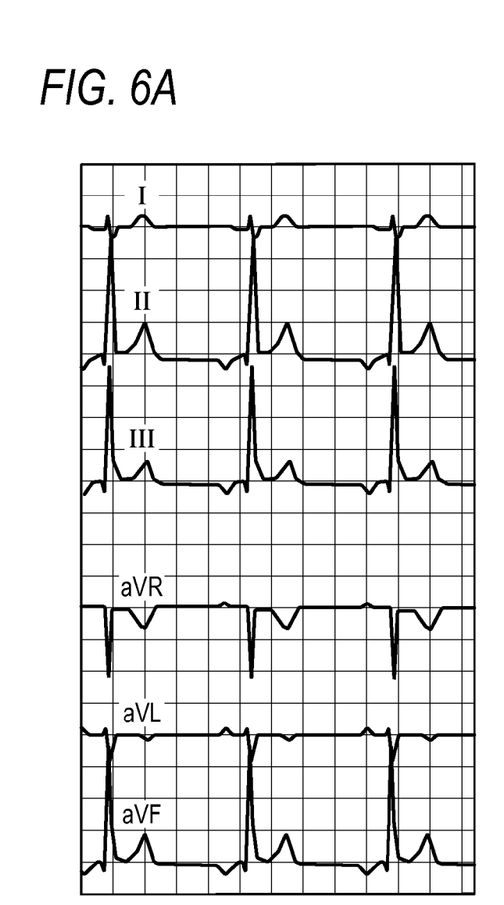
Figure 6B:
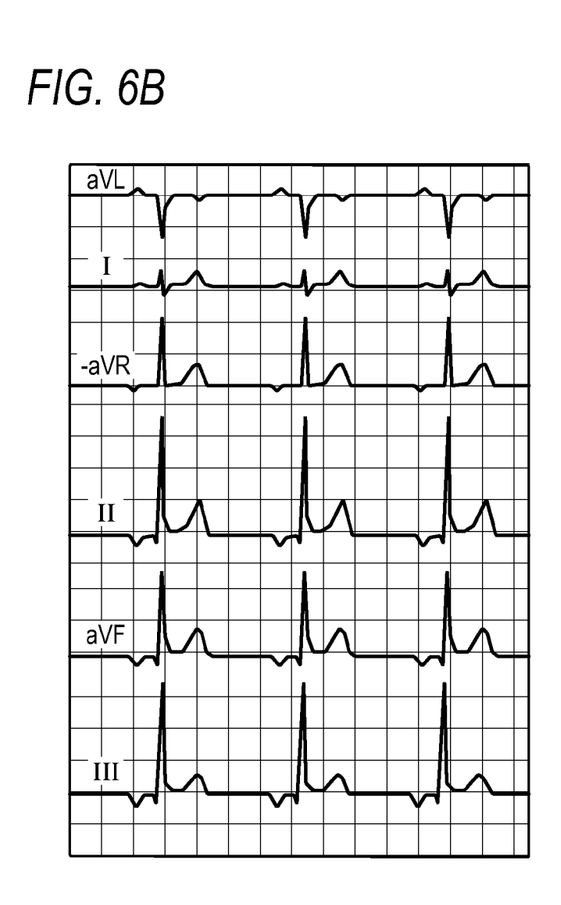

In FIG. 6A, an example in which an electrocardiogram of the "atrioventricular nodal rhythm" is displayed in a standard 12-lead mode is shown. In this state, the arranging-order candidates as shown in FIG. 5 can be displayed by the arranging-order candidate displaying control unit 35 and inputting for designating (selecting) any one of case information and arranging-order candidate information displayed as described above by the arranging instruction unit 33 can be performed. Herein, for example, if the Cabrera lead mode is selected, displaying the Cabrera lead mode as shown in FIG. 6B is performed, and also because the characteristic of the electrocardiogram waveforms is "inversion of polarity in a P-wave after –aVR lead", an electrocardiogram shown in FIG. 6B can be easily determined to be an electrocardiogram of the "atrioventricular nodal rhythm" by visual observation.

Next, a third embodiment will be described. In an electrocardiogram display device according to the third embodiment, the detecting unit 36 for detecting whether a screen of the display unit is arranged to be vertically or horizontally long is equipped therein, and the displaying control unit 34 creates and displays one screen image, in which an electrocardiogram waveform of each lead is displayed in an arranging order changed depending on a result detected by the detecting unit, on the display unit 41.

Figure 7:
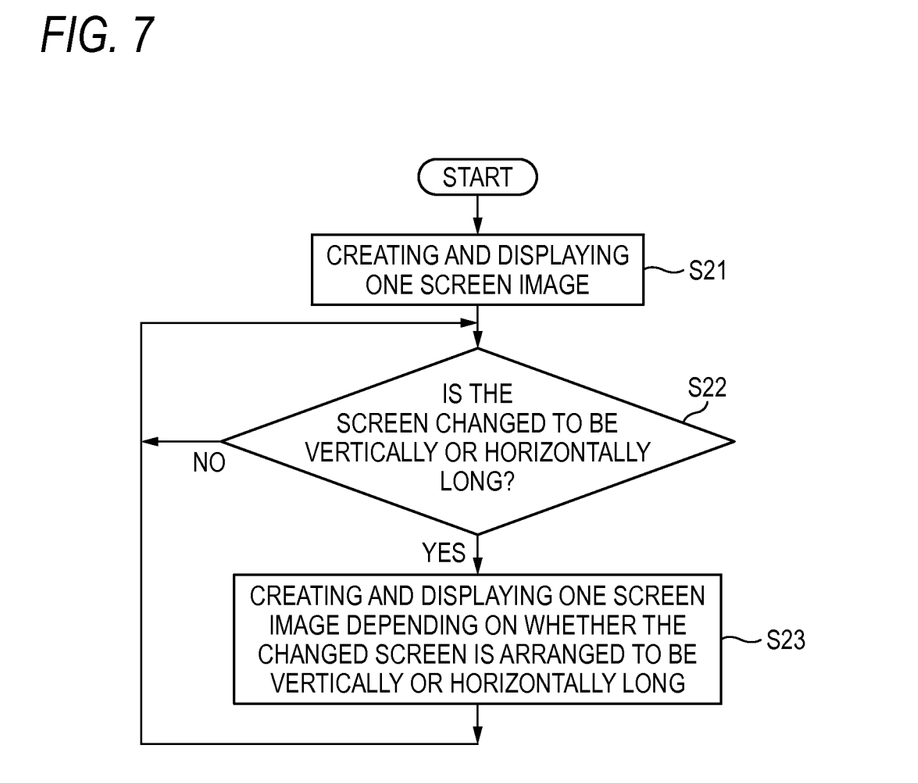
FIG. 7 is a flow chart showing operations of the embodiment of the electrocardiogram display device according to the presently disclosed subject matter, illustrating operations depending on whether the screen is arranged to be vertically or horizontally long.

Specifically, the electrocardiogram display device is operated, for example, as shown in a flow chart of FIG. 7. For example, in the case where the electrocardiogram display device is operated as shown in the flow chart of FIG. 3, a program corresponding to the flow chart of FIG. 7 is also run, and also one screen image is created and displayed in an arranging order corresponding to selection from an arranging-order candidate display (S21). In a step S22 following the step S21, whether the screen is changed to be vertically or horizontally long is detected by the detecting unit 36 (S22).

Figure 8:
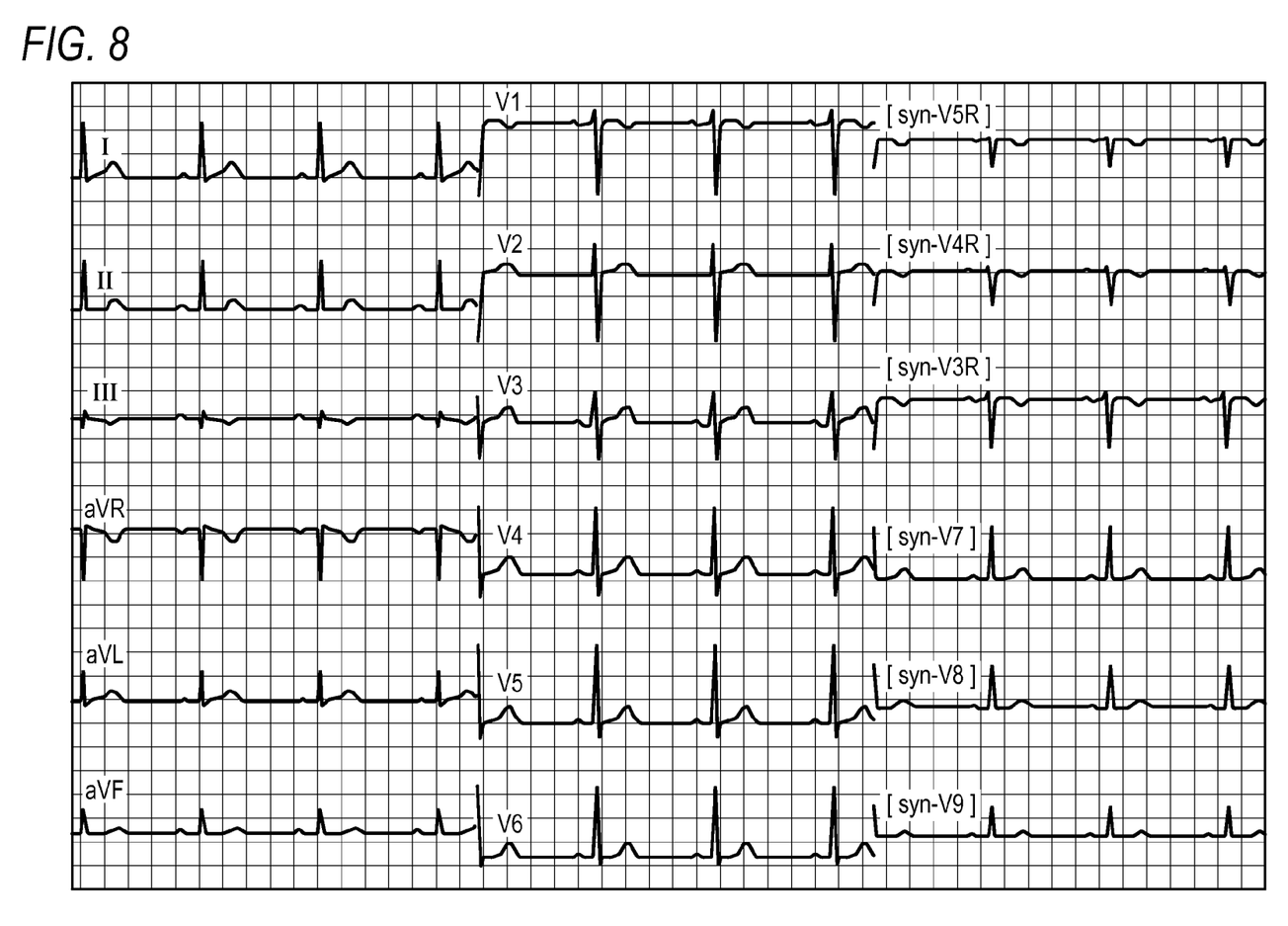
FIG. 8 is a view showing a display example of electrocardiogram waveforms when performing operations in accordance with the flow chart of FIG. 7, illustrating a case where a screen thereof is arranged to be horizontally long.

For example, in a case where a change from a horizontally long screen to a vertically long screen is detected in the step S22, it is, for example, assumed that the horizontally long screen is displayed in a general synthesized 18-lead mode shown in FIG. 8. In this case, when the change from the horizontally long screen to the vertically long screen is made, as shown in FIG. 9, a display image in which each lead is vertically arranged one by one can be displayed on the display unit 41 (S23).

Figure 9:
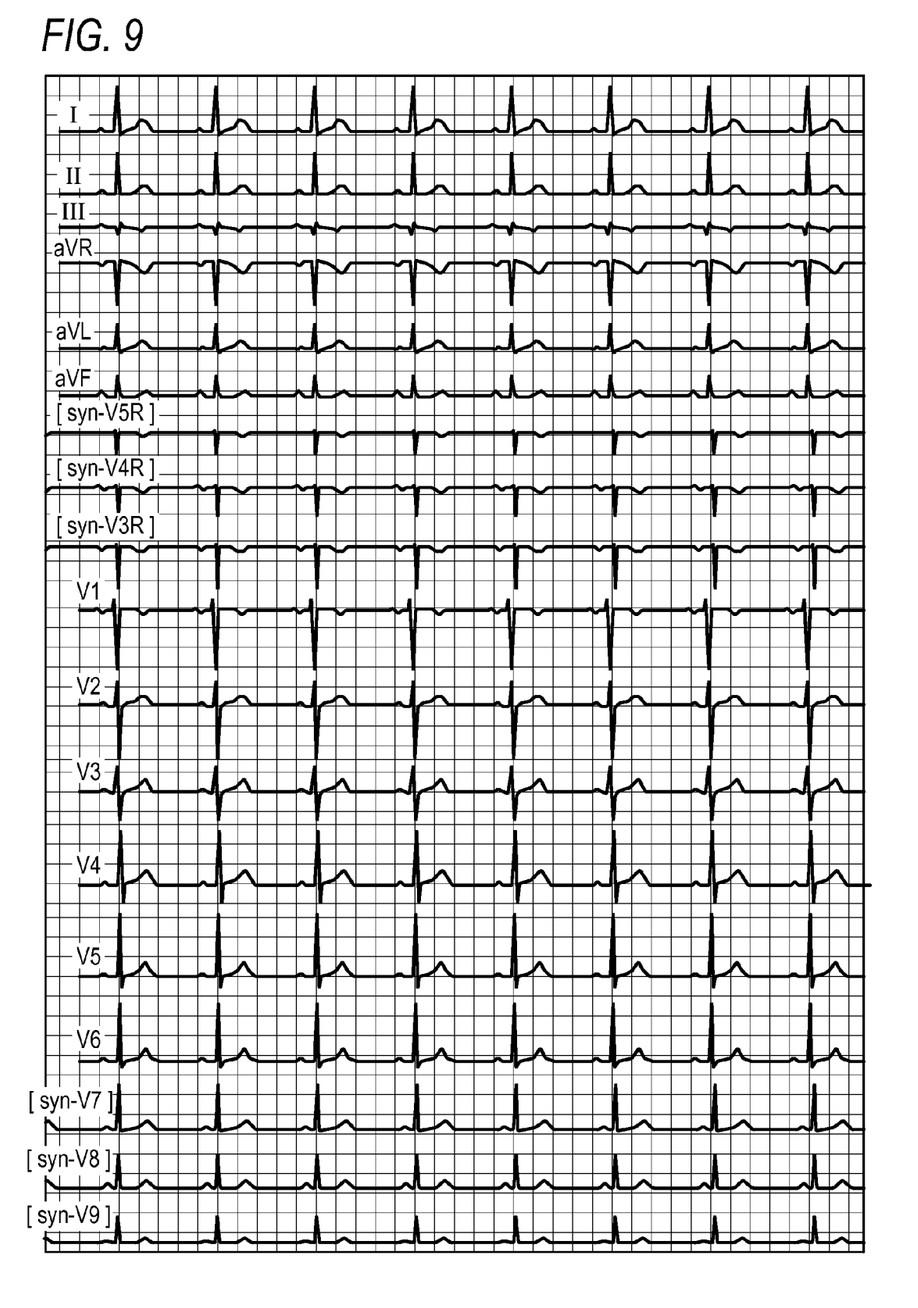
FIG. 9 is a display example of a case where the screen is changed to be vertically long from the displayed state of FIG. 8 and "vectorial arrangement" is selected.

Meanwhile, an arranging order of chest leads is changed in FIG. 9. Namely, an item "vectorial arrangement" is displayed as the arranging-order candidate information described in the second embodiment, and as the item is selected, one screen image is displayed in the vectorial arrangement by a vertically long image as shown in FIG. 9. Due to such displaying, conduction state of excitement can be easily visually recognized. In order to display the item "vectorial arrangement", the following can be performed. Specifically, as described in the first embodiment, a "display switching" button B is displayed on a corner of the screen. Also, the item "vectorial arrangement" is displayed on a pop-up window displayed by operating the button, and then the item "vectorial arrangement" is selected. Additionally, the order of chest leads in accordance with the "vectorial arrangement" is V5R, V4R, V3R, V1, V2, V3, V4, V5, V6, V7, V8 and V9 (the prefix "syn-" in Syn-V5R and the like of FIG. 9 means that the corresponding waveform is a synthesized electrocardiogram waveform). Due to such an arrangement, cases such as infarction of the right ventricular posterior wall can be appropriately captured.

Figure 10:
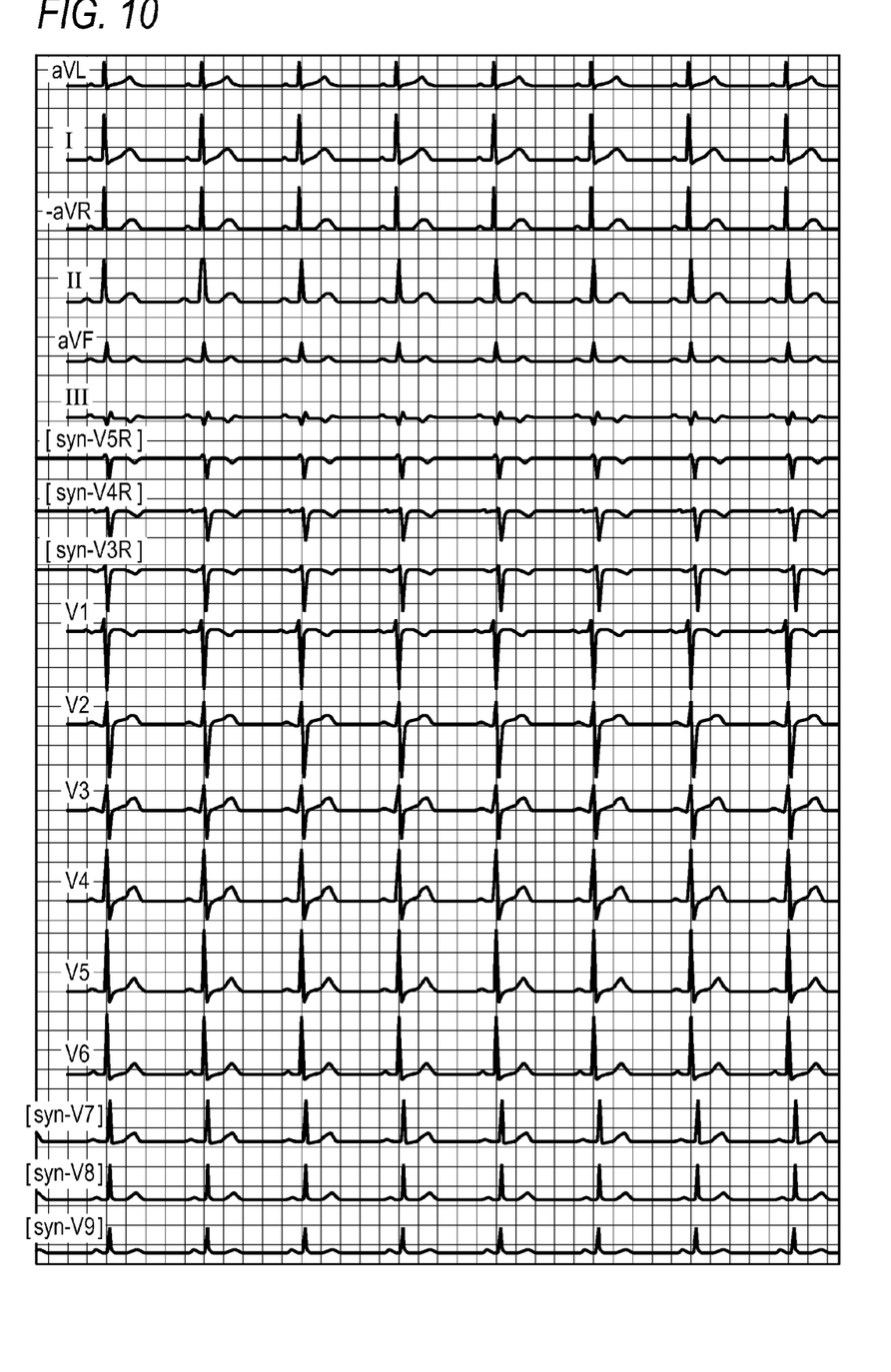
FIG. 10 is a display example of a case where the screen is changed to be vertically long from the displayed state of FIG. 8 and "Cabrera lead arrangement" is selected.

Similarly to FIG. 9, FIG. 10 shows an arrangement when a horizontal screen display mode of general synthesized 18-leads shown in FIG. 8 is changed to a vertical screen display mode. In this example, an arranging order of chest leads follows the "vectorial arrangement" and an arranging order of extremity leads follows the "Cabrera lead arrangement" Although the method of manually setting the arranging order is described in the foregoing description of FIGS. 9 and 10, the presently disclosed subject matter may be configured to automatically determine the arranging order of FIG. 9 or 10 when a change from the horizontal screen to the vertical screen is detected in the step S22.

The electrocardiogram display device according to the embodiment can arrange the electrocardiogram waveform of each lead in a corresponding arranging order in response to instruction of the arranging instruction unit, which is configured to instruct an arranging order of the electrocardiogram waveform of each lead by performing inputting, to create and display one screen image on the display mean. Accordingly, the electrocardiogram waveform of each lead can be arranged in a desired arranging order and thus usability thereof can be enhanced.

Also, the electrocardiogram display device according to the embodiment can display case information and arranging-order candidate information in pairs on the display unit and can appropriately change and display an arrangement of the electrocardiogram waveform of each lead from one, which is currently displayed, to another by performing inputting for designating any one of the displayed case information and arranging-order candidate information by the arranging instruction unit. Accordingly, it is possible to display the electrocardiogram waveform of each lead in a suitable arrangement while comparing relationships between case information and arranging-order candidate information.

The electrocardiogram display device according to the embodiment can arrange the electrocardiogram waveform of each lead in a corresponding arranging order in response to instruction of the arranging instruction unit, which is configured to instruct an arranging order of leads suitable to represent a case based on an analysis result of the electrocardiogram analyzing unit. Accordingly, the case can be instantly examined and evaluated in detail.

Further, the electrocardiogram display device according to the embodiment has a detecting unit that detects whether a screen of the display unit is arranged to be vertically or horizontally long, and the displaying control unit is configured to create and display one screen image, in which the electrocardiogram waveform of each lead is displayed in an arranging order changed depending on a result detected by the detecting unit. Accordingly, in a case of a device in which a screen thereof can be changed to be vertically or horizontally long, an arranging order of the electrocardiogram waveform of each lead can be changed and arranged by only changing the screen to be vertically or horizontally long, and this is effective to understand the electrocardiogram.

What is claimed is:

1. An electrocardiogram display device comprising:
   an electrocardiogram waveform generating unit that generates electrocardiogram waveforms of a plurality of leads based on electrocardiogram data of each of the leads;
   an arranging instruction unit that instructs an arranging order of the electrocardiogram waveform of each lead by performing inputting;
   a display unit;
   a displaying control unit that arranges the electrocardiogram waveform of each lead in a corresponding arranging order in response to instruction of the arranging instruction unit to create and display one screen image on the display unit; and
   an arranging-order candidate displaying control unit that changes the one screen image on the display unit into a modified one screen image showing the electrocardiogram waveform of each lead in a given combination, based on arranging-order candidate information which includes one or more arranging-order candidates.

2. The electrocardiogram display device according to claim 1 further comprising:
   an electrocardiogram analyzing unit that analyze the electrocardiogram waveforms of each lead;
   wherein the arranging-order candidate displaying control unit displays the arranging-order candidate information based on an analysis result of the electrocardiogram analyzing unit,
   wherein the arrangement instruction unit is configured to perform inputting for designating any one of the displayed arranging-order candidate information.

3. The electrocardiogram display device according to claim 2,
   wherein the arranging-order candidate displaying control unit is configured to display case information and the arranging-order candidate information in pairs on the display unit,
   wherein the arrangement instruction unit is configured to perform inputting for designating any one of the displayed case information and arranging-order candidate information.

4. The electrocardiogram display device according to claim 3 further comprising a detecting unit that detects whether a screen of the display unit is arranged to be vertically or horizontally long,
   wherein the displaying control unit is configured to create and display one screen image, in which the electrocardiogram waveform of each lead is displayed in an arranging order changed depending on a result detected by the detecting unit, on the display unit.

5. The electrocardiogram display device according to claim 2,
   wherein the arranging-order candidate information is displayed so that arranging-order candidate information of one screen image, which is currently displayed, can be distinguished from arranging-order candidate information of one screen image, which is not currently displayed.

6. The electrocardiogram display device according to claim 5 further comprising a detecting unit that detects whether a screen of the display unit is arranged to be vertically or horizontally long,
   wherein the displaying control unit is configured to create and display one screen image, in which the electrocardiogram waveform of each lead is displayed in an arranging order changed depending on a result detected by the detecting unit, on the display unit.

7. The electrocardiogram display device according to claim 2 further comprising a detecting unit that detects whether a screen of the display unit is arranged to be vertically or horizontally long,
   wherein the displaying control unit is configured to create and display one screen image, in which the electrocardiogram waveform of each lead is displayed in an arranging order changed depending on a result detected by the detecting unit, on the display unit.

8. The electrocardiogram display device according to claim 1 further comprising a detecting unit that detects whether a screen of the display unit is arranged to be vertically or horizontally long,
   wherein the displaying control unit is configured to create and display one screen image, in which the electrocardiogram waveform of each lead is displayed in an arranging order changed depending on a result detected by the detecting unit, on the display unit.

9. The electrocardiogram display device according to claim 1, wherein the arranging-order candidates include at least one of vectorial arranging and Cabrera lead arrangement.

10. The electrocardiogram display device of claim 1, wherein the arranging order candidate displaying control unit displays the arranging order candidate information in the one screen image on the display unit.

11. An electrocardiogram display device comprising:
    an electrocardiogram waveform generating unit that generates electrocardiogram waveforms of a plurality of leads based on electrocardiogram data of each of the leads;

an electrocardiogram analyzing unit that analyzes the electrocardiogram waveforms of each lead;

an arranging instruction unit that instructs an arranging order of leads suitable to represent a case based on an analysis result of the electrocardiogram analyzing unit;

a display unit;

a displaying control unit that arranges the electrocardiogram waveform of each lead in a corresponding arranging order in response to instruction of the arranging instruction unit to create and display one screen image on the display unit; and an arranging-order candidate displaying control unit that changes the one screen image on the display unit into one screen image having the electrocardiogram waveform of each lead with a given combination based on arranging-order candidate information which includes one or more arranging-order candidates.

12. The electrocardiogram display device according to claim 11 further comprising a detecting unit that detects whether a screen of the display unit is arranged to be vertically or horizontally long, wherein the displaying control unit is configured to create and display one screen image, in which the electrocardiogram waveform of each lead is displayed in an arranging order changed depending on a result detected by the detecting unit, on the display unit.

13. The electrocardiogram display device according to claim 11, wherein the arranging-order candidates include at least one of vectorial arranging and Cabrera lead arrangement.

14. An electrocardiogram display device comprising:

a waveform generating unit that generates waveforms from a plurality of leads based on electrocardiogram data detected by each of the leads;

an arrangement selection unit comprising a set of candidate arrangements, with each candidate arrangement corresponding to an ordering or arrangement of the waveforms, a display unit comprising a screen;

a display control unit that controls the display unit to cause the screen to display a composite image of the waveforms according to the candidate arrangement specified by the arrangement selection unit;

an electrocardiogram analyzing unit that analyzes the electrocardiogram data detected by each lead in order to identify possible cardiovascular conditions; and an arrangement control unit that, in response to an analysis result of the electrocardiogram analyzing unit, compiles a chosen subset of candidate arrangements, such that each candidate arrangement within the chosen subset highlights one of the possible cardiovascular conditions identified by the electrocardiogram analyzing unit;

wherein the arrangement selection unit, in response to a user input, allows a candidate arrangement to be specified from the chosen subset of candidate arrangements.

15. The electrocardiogram display device of claim 14, wherein the arrangement control unit, in response to a user query, displays the chosen subset on the screen.

* * * * *